US009624529B2

(12) United States Patent
Oyler et al.

(10) Patent No.: US 9,624,529 B2
(45) Date of Patent: Apr. 18, 2017

(54) N-END RULE PROTEASE ACTIVITY INDICATION METHODS AND USES THEREOF

(71) Applicant: Synaptic Research, LLC, Baltimore, MD (US)

(72) Inventors: George A. Oyler, Baltimore, MD (US); Yien Che Tsai, Frederick, MD (US)

(73) Assignee: SYNAPTIC RESEARCH, LLC, Baltimore, MD (US)

( * ) Notice: Subject to any disclaimer, the term of this patent is extended or adjusted under 35 U.S.C. 154(b) by 0 days.

(21) Appl. No.: 14/606,352

(22) Filed: Jan. 27, 2015

(65) Prior Publication Data
US 2015/0329896 A1 Nov. 19, 2015

Related U.S. Application Data

(62) Division of application No. 13/159,284, filed on Jun. 13, 2011, now Pat. No. 8,940,482.

(60) Provisional application No. 61/354,041, filed on Jun. 11, 2010.

(51) Int. Cl.
*C12Q 1/00* (2006.01)
*C12Q 1/68* (2006.01)
*C12Q 1/66* (2006.01)
*C12Q 1/37* (2006.01)

(52) U.S. Cl.
CPC ............. *C12Q 1/66* (2013.01); *C12Q 1/37* (2013.01); *G01N 2333/33* (2013.01); *G01N 2333/952* (2013.01); *G01N 2500/10* (2013.01)

(58) Field of Classification Search
CPC ........... G01N 2333/33; G01N 2500/10; G01N 33/5005; C12Q 1/66
USPC ........................................ 435/8, 23, 252.3
See application file for complete search history.

(56) References Cited

U.S. PATENT DOCUMENTS

| | | | | |
|---|---|---|---|---|
| 7,632,917 B2 * | 12/2009 | Kincaid | ............... | C07K 14/705 424/239.1 |
| 8,492,109 B2 * | 7/2013 | Oyler | ..................... | C12N 9/52 435/24 |
| 8,940,482 B1 * | 1/2015 | Oyler | ..................... | C12Q 1/37 435/6.1 |
| 9,274,121 B2 * | 3/2016 | Atapattu | .............. | G01N 33/582 |
| 2005/0019338 A1 * | 1/2005 | Holland | ............. | A61K 49/0004 424/184.1 |
| 2006/0233836 A1 * | 10/2006 | Kincaid | ............... | C07K 14/705 424/239.1 |
| 2010/0222555 A1 * | 9/2010 | Dessain | ............. | C07K 16/1282 530/387.3 |
| 2011/0143362 A1 * | 6/2011 | Oyler | ................. | C12N 15/1034 435/6.18 |
| 2016/0069862 A1 * | 3/2016 | Tucker | ............... | G01N 33/5005 435/23 |

FOREIGN PATENT DOCUMENTS

WO 2004/031355 * 4/2004

OTHER PUBLICATIONS

Sharma, M et al, Nature, Cell Biology, vol. 13(1), Jan. 2011, pp. 30-39 plus methods pages and spplementary informations pp. 1-7, CSPalpha promotes SNARE-complex assembly by chaperoning SNP-25 during synaptic activity.*

* cited by examiner

*Primary Examiner* — Albert Navarro
*Assistant Examiner* — Mark Navarro
(74) *Attorney, Agent, or Firm* — Whiteford, Taylor & Preston, LLP; Peter J. Davis

(57) ABSTRACT

A cell based assay for detection for protease activity is disclosed. In the assay a cell is engineered to express a protease substrate with at least one label, preferably on its C-terminus. Cleavage of the substrate by the protease that recognizes it results in a C-terminal fragment and a N-terminal fragment, where the fragment having the label is subject to ubiquitin proteasome degradation. The assay measures the disappearance of the label due to degradation of the fragment to which it is attached. A cell free assay is also described for detection of protease activity. In the cell free assay, the protease substrate is expressed in a solution that includes the elements of the ubiquitin proteasome pathway for degradation of the fragment. The assay measures the disappearance of the label attached to the fragment that results from cleavage by the protease.

4 Claims, 3 Drawing Sheets a.

| Lane | Sample |
|---|---|
| 1 | Ladder |
| 2 | CFP-BoNT/LcA |
| 3 | SNAP25-FRET |
| 4 | SNAP25-FRET + CFP-BoNT/LcA |

Lane 1: Ladder

Lane 2: Positive control showing CFP-BoNT/LcA band at 83kDa

Lane 3: Positive control showing SBP-CFP-SNAP25-Venus-BD-NfkB band at 125kDa

Lane 4: Test showing the full length SBP-CFP-SNAP25-Venus-BD-NfkB band disappearing after cleavage by BoNT/LcA and N terminal cleaved product seen at 57kDa present on western blot using anti-GFP antibody. There is no C-terminal cleavage fragment containing Venus present on Western blot due to degradation.

SEQUENCE LISTING

```
<160> NUMBER OF SEQ ID NOS: 4

<210> SEQ ID NO 1
<211> LENGTH: 2295
<212> TYPE: DNA
<213> ORGANISM: Artificial Sequence
<220> FEATURE:
<223> OTHER INFORMATION: Fusion protein between SNAP 25 and Luciferase

<400> SEQUENCE: 1
atggactaca aagaccatga cggtatggcc gaagacgcag acatgcgcaa tgagctggag      60
gagatgcaga ggagggctga ccagctggct gatgagtccc tggaaagcac ccgtcgcatg     120
ctgcagctgg ttgaagagag taaagatgct ggcatcagga ctttggttat gttggatgag     180
caaggcgaac aactggaacg cattgaggaa gggatggacc aaatcaataa ggacatgaaa     240
gaagcagaaa agaatttgac ggacctagga aaattctgcg gctttgtgt gtgtccctgt      300 aacaagctta atccagtga tgcttacaaa aaagcctggg gcaataatca ggatggagta     360
gtggccagcc agcctgcccg tgtggtggat aacgggagc agatggccat cagtggtggc     420
ttcatccgca gggtaacaaa tgatgcccgg gaaaatgaga tggatgagaa cctggagcag     480
gtgagcggca tcatcggaaa cctccgccat atggctctag acatgggcaa tgagattgac     540
acccagaatc gccagatcga caggatcatg gagaaggctg attccaacaa aaccagaatt     600
gatgaagcca accaacgtgc aacaaagatg ctgggaagtg gtaccgaaga cgccaaaaac     660
ataaagaaag gcccggcgcc attctatcct ctagaggatg gaaccgctgg agagcaactg     720
cataaggcta tgaagagata cgccctggtt cctgaacaa ttgcttttac agatgcacat     780
atcgaggtga acatcacgta cgcggaatac ttcgaaatgt ccgttcggtt ggcagaagct     840
atgaaacgat atgggctgaa tacaaatcac agaatcgtcg tatgcagtga aaactctctt     900
```

```
caattcttta tgccggtgtt gggcgcgtta tttatcggag ttgcagttgc gcccgcgaac    960
gacatttata atgaacgtga attgctcaac agtatgaaca tttcgcagcc taccgtagtg   1020 tttgttttcca aaaggggtt gcaaaaaatt ttgaacgtgc aaaaaaaatt accaataatc   1080
cagaaaatta ttatcatgga ttctaaaacg gattaccagg gatttcagtc gatgtacacg   1140
ttcgtcacat ctcatctacc tcccggtttt aatgaatacg attttgtacc agagtccttt   1200
gatcgtgaca aaacaattgc actgataatg aattcctctg gatctactgg gttacctaag   1260
ggtgtggccc ttccgcatag aactgcctgc gtcagattct cgcatgccag agatcctatt   1320
tttggcaatc aaatcattcc ggatactgcg attttaagtg ttgttccatt ccatcacggt   1380
tttggaatgt ttactacact cggatatttg atatgtggat ttcgagtcgt cttaatgtat   1440
agatttgaag aagagctgtt tttacgatcc cttcaggatt acaaaattca aagtgcgttg   1500
ctagtaccaa ccctattttc attcttcgcc aaaagcactc tgattgacaa atacgattta   1560
tctaatttac acgaaattgc ttctgggggc gcacctcttt cgaaagaagt cggggaagcg   1620
gttgcaaaac gcttccatct tccagggata cgacaaggat atgggctcac tgagactaca   1680
tcagctattc tgattacacc cgaggggat gataaaccgg gcgcggtcgg taaagttgtt   1740 ccatttttg aagcgaaggt tgtggatctg gataccggga aaacgctggg cgttaatcag   1800
agaggcgaat tatgtgtcag aggacctatg attatgtccg gttatgtaaa caatccggaa   1860
gcgaccaacg ccttgattga caaggatgga tggctacatt ctggagacat agcttactgg   1920
gacgaagacg aacacttctt catagttgac cgcttgaagt cttaattaa atacaaagga   1980 tatcaggtgg cccccgctga attggaatcg atattgttac aacaccccaa catcttcgac   2040
gcgggcgtgg caggtcttcc cgacgatgac gccggtgaac ttcccgccgc cgttgttgtt   2100
ttggagcacg gaaagacgat gacggaaaaa gagatcgtgg attacgtcgc cagtcaagta   2160
acaaccgcga aaaagttgcg cggaggagtt gtgtttgtgg acgaagtacc gaaaggtctt   2220
accggaaaac tcgacgcaag aaaaatcaga gagatcctca taaaggccaa gaagggcgga   2280
aagtccaaat tgtaa                                                   2295
```

<210> SEQ ID NO 2
<211> LENGTH: 764
<212> TYPE: PRT
<213> ORGANISM: Artificial Sequence
<220> FEATURE:
<223> OTHER INFORMATION: Snap 25 Luc Fusion Peptide

<400> SEQUENCE: 2

```
Met Asp Tyr Lys Asp His Asp Gly Met Ala Glu Asp Ala Asp Met Arg
1               5                   10                  15

Asn Glu Leu Glu Glu Met Gln Arg Arg Ala Asp Gln Leu Ala Asp Glu
            20                  25                  30

Ser Leu Glu Ser Thr Arg Arg Met Leu Gln Leu Val Glu Glu Ser Lys
        35                  40                  45

Asp Ala Gly Ile Arg Thr Leu Val Met Leu Asp Glu Gln Gly Glu Gln
    50                  55                  60

Leu Glu Arg Ile Glu Glu Gly Met Asp Gln Ile Asn Lys Asp Met Lys
65                  70                  75                  80

Glu Ala Glu Lys Asn Leu Thr Asp Leu Gly Lys Phe Cys Gly Leu Cys
                85                  90                  95

Val Cys Pro Cys Asn Lys Leu Lys Ser Ser Asp Ala Tyr Lys Lys Ala
            100                 105                 110
```

-continued

```
Trp Gly Asn Asn Gln Asp Gly Val Ala Ser Gln Pro Ala Arg Val
            115                 120                 125
Val Asp Glu Arg Glu Gln Met Ala Ile Ser Gly Gly Phe Ile Arg Arg
130                 135                 140
Val Thr Asn Asp Ala Arg Glu Asn Glu Met Asp Glu Asn Leu Glu Gln
145                 150                 155                 160
Val Ser Gly Ile Ile Gly Asn Leu Arg His Met Ala Leu Asp Met Gly
            165                 170                 175
Asn Glu Ile Asp Thr Gln Asn Arg Gln Ile Asp Arg Ile Met Glu Lys
            180                 185                 190
Ala Asp Ser Asn Lys Thr Arg Ile Asp Glu Ala Asn Gln Arg Ala Thr
            195                 200                 205
Lys Met Leu Gly Ser Gly Thr Glu Asp Ala Lys Asn Ile Lys Lys Gly
            210                 215                 220
Pro Ala Pro Phe Tyr Pro Leu Glu Asp Gly Thr Ala Gly Glu Gln Leu
225                 230                 235                 240
His Lys Ala Met Lys Arg Tyr Ala Leu Val Pro Gly Thr Ile Ala Phe
            245                 250                 255
Thr Asp Ala His Ile Glu Val Asn Ile Thr Tyr Ala Glu Tyr Phe Glu
            260                 265                 270
Met Ser Val Arg Leu Ala Glu Ala Met Lys Arg Tyr Gly Leu Asn Thr
            275                 280                 285
Asn His Arg Ile Val Val Cys Ser Glu Asn Ser Leu Gln Phe Phe Met
            290                 295                 300
Pro Val Leu Gly Ala Leu Phe Ile Gly Val Ala Val Ala Pro Ala Asn
305                 310                 315                 320
Asp Ile Tyr Asn Glu Arg Glu Leu Leu Asn Ser Met Asn Ile Ser Gln
            325                 330                 335
Pro Thr Val Val Phe Val Ser Lys Lys Gly Leu Gln Lys Ile Leu Asn
            340                 345                 350
Val Gln Lys Lys Leu Pro Ile Ile Gln Lys Ile Ile Ile Met Asp Ser
            355                 360                 365
Lys Thr Asp Tyr Gln Gly Phe Gln Ser Met Tyr Thr Phe Val Thr Ser
            370                 375                 380
His Leu Pro Pro Gly Phe Asn Glu Tyr Asp Phe Val Pro Glu Ser Phe
385                 390                 395                 400
Asp Arg Asp Lys Thr Ile Ala Leu Ile Met Asn Ser Ser Gly Ser Thr
            405                 410                 415
Gly Leu Pro Lys Gly Val Ala Leu Pro His Arg Thr Ala Cys Val Arg
            420                 425                 430
Phe Ser His Ala Arg Asp Pro Ile Phe Gly Asn Gln Ile Ile Pro Asp
            435                 440                 445
Thr Ala Ile Leu Ser Val Val Pro Phe His His Gly Phe Gly Met Phe
            450                 455                 460
Thr Thr Leu Gly Tyr Leu Ile Cys Gly Phe Arg Val Val Leu Met Tyr
465                 470                 475                 480
Arg Phe Glu Glu Glu Leu Phe Leu Arg Ser Leu Gln Asp Tyr Lys Ile
            485                 490                 495
Gln Ser Ala Leu Leu Val Pro Thr Leu Phe Ser Phe Phe Ala Lys Ser
            500                 505                 510
Thr Leu Ile Asp Lys Tyr Asp Leu Ser Asn Leu His Glu Ile Ala Ser
            515                 520                 525
```

Gly Gly Ala Pro Leu Ser Lys Glu Val Gly Glu Val Ala Lys Arg
530             535                 540

Phe His Leu Pro Gly Ile Arg Gln Gly Tyr Gly Leu Thr Glu Thr Thr
545                 550                 555                 560

Ser Ala Ile Leu Ile Thr Pro Glu Gly Asp Asp Lys Pro Gly Ala Val
                565                 570                 575

Gly Lys Val Val Pro Phe Phe Glu Ala Lys Val Val Asp Leu Asp Thr
            580                 585                 590

Gly Lys Thr Leu Gly Val Asn Gln Arg Gly Glu Leu Cys Val Arg Gly
            595                 600                 605

Pro Met Ile Met Ser Gly Tyr Val Asn Asn Pro Glu Ala Thr Asn Ala
610                 615                 620

Leu Ile Asp Lys Asp Gly Trp Leu His Ser Gly Asp Ile Ala Tyr Trp
625                 630                 635                 640

Asp Glu Asp Glu His Phe Phe Ile Val Asp Arg Leu Lys Ser Leu Ile
                645                 650                 655

Lys Tyr Lys Gly Tyr Gln Val Ala Pro Ala Glu Leu Glu Ser Ile Leu
            660                 665                 670

Leu Gln His Pro Asn Ile Phe Asp Ala Gly Val Ala Gly Leu Pro Asp
        675                 680                 685

Asp Asp Ala Gly Glu Leu Pro Ala Ala Val Val Val Leu Glu His Gly
690                 695                 700

Lys Thr Met Thr Glu Lys Glu Ile Val Asp Tyr Val Ala Ser Gln Val
705                 710                 715                 720

Thr Thr Ala Lys Lys Leu Arg Gly Gly Val Val Phe Val Asp Glu Val
                725                 730                 735

Pro Lys Gly Leu Thr Gly Lys Leu Asp Ala Arg Lys Ile Arg Glu Ile
            740                 745                 750

Leu Ile Lys Ala Lys Lys Gly Gly Lys Ser Lys Leu
            755                 760

<210> SEQ ID NO 3
<211> LENGTH: 2295
<212> TYPE: DNA
<213> ORGANISM: Artificial Sequence
<220> FEATURE:
<223> OTHER INFORMATION: Fusion protein between mutated SNAP25 and
      Luciferase

<400> SEQUENCE: 3
atggactaca aagaccatga cggtatggcc gaggacgcag acatgcgcaa tgagctggag      60
gagatgcaga ggagggctga ccagctggct gatgagtccc tggaaagcac ccgtcgcatg     120
ctgcagctgg ttgaagagag taaagatgct ggcatcagga cttttggtta tgttggatga     180
caaggcgaac aactggaacg cattgaggaa gggatggacc aaatcaataa ggacatgaaa     240
gaagcagaaa agaatttgac ggacctagga aaattctgcg gctttgtgt gtgtccctgt     300 aacaagctta atccagtga tgcttacaaa aaagcctggg gcaataatca ggatggagta     360
gtggccagcc agcctgcccg tgtggtggat gaacgggagc agatggccat cagtggtggc     420
ttcatccgca gggtaacaaa tgatgcccgg gaaaatgaga tggatgagaa cctggagcag     480
gtgagcggca tcatcggaaa cctccgccat atggctctag acatgggcaa tgagattgac     540
acccagaatc gccagattaa gaggatcatg gagaaggctg attccaacaa aaccagaatt     600
gatgaagcca accaaactgc aacaaagatg ctgggaagtg gtaccgaaga cgccaaaaac     660
ataaagaaag cccggcgcc attctatcct ctagaggatg aaccgctgg agagcaactg     720

```
cataaggcta tgaagagata cgccctggtt cctggaacaa ttgcttttac agatgcacat      780
atcgaggtga acatcacgta cgcggaatac ttcgaaatgt ccgttcggtt ggcagaagct      840
atgaaacgat atgggctgaa tacaaatcac agaatcgtcg tatgcagtga aaactctctt      900
caattcttta tgccggtgtt gggcgcgtta tttatcggag ttgcagttgc gcccgcgaac      960
gacatttata tgaacgtga attgctcaac agtatgaaca tttcgcagcc taccgtagtg     1020
tttgtttcca aaaggggtt gcaaaaaatt ttgaacgtgc aaaaaaaatt accaataatc     1080
cagaaaatta ttatcatgga ttctaaaacg gattaccagg gatttcagtc gatgtacacg     1140
ttcgtcacat ctcatctacc tcccggtttt aatgaatacg attttgtacc agagtccttt     1200
gatcgtgaca aaacaattgc actgataatg aattcctctg gatctactgg gttacctaag     1260
ggtgtggccc ttccgcatag aactgcctgc gtcagattct cgcatgccag agatcctatt     1320
tttggcaatc aaatcattcc ggatactgcg attttaagtg ttgttccatt ccatcacggt     1380 tttgaatgt ttactacact cggatatttg atatgtggat ttcgagtcgt cttaatgtat     1440
agatttgaag aagagctgtt tttacgatcc cttcaggatt acaaaattca aagtgcgttg     1500
ctagtaccaa ccctatttc attcttcgcc aaaagcactc tgattgacaa atacgattta     1560
tctaatttac acgaaattgc ttctgggggc gcacctcttt cgaaagaagt cggggaagcg     1620
gttgcaaaac gcttccatct tccagggata cgacaaggat atgggctcac tgagactaca     1680
tcagctattc tgattacacc cgagggggat gataaaccgg gcgcggtcgg taaagttgtt     1740 ccatttttg aagcgaaggt tgtggatctg gataccggga aaacgctggg cgttaatcag     1800
agaggcgaat tatgtgtcag aggacctatg attatgtccg gttatgtaaa caatccggaa     1860
gcgaccaacg ccttgattga caaggatgga tggctacatt ctggagacat agcttactgg     1920
gacgaagacg aacacttctt catagttgac cgcttgaagt ctttaattaa atacaaagga     1980
tatcaggtgg cccccgctga attggaatcg atattgttac aacacccaa catcttcgac     2040 gcgggcgtgg caggtcttcc cgacgatgac gccggtgaac ttcccgccgc cgttgttgtt     2100
ttggagcacg gaaagacgat gacggaaaaa gagatcgtgg attacgtcgc cagtcaagta     2160
acaaccgcga aaaagttgcg cggaggagtt gtgtttgtgg acgaagtacc gaaaggtctt     2220
accggaaaac tcgacgcaag aaaaatcaga gagatcctca taaaggccaa gaagggcgga     2280
aagtccaaat tgtaa                                                     2295
```

<210> SEQ ID NO 4
<211> LENGTH: 764
<212> TYPE: PRT
<213> ORGANISM: Artificial Sequence
<220> FEATURE:
<223> OTHER INFORMATION: Fusion peptide of mutated SNAP-25 and
      Luciferase

<400> SEQUENCE: 4

Met Asp Tyr Lys Asp His Asp Gly Met Ala Glu Asp Ala Asp Met Arg
1               5                   10                  15

Asn Glu Leu Glu Glu Met Gln Arg Arg Ala Asp Gln Leu Ala Asp Glu
            20                  25                  30

Ser Leu Glu Ser Thr Arg Arg Met Leu Gln Leu Val Glu Glu Ser Lys
        35                  40                  45

Asp Ala Gly Ile Arg Thr Leu Val Met Leu Asp Glu Gln Gly Glu Gln
    50                  55                  60

Leu Glu Arg Ile Glu Glu Gly Met Asp Gln Ile Asn Lys Asp Met Lys

```
            65                  70                  75                  80
        Glu Ala Glu Lys Asn Leu Thr Asp Leu Gly Lys Phe Cys Gly Leu Cys
                        85                  90                  95
        Val Cys Pro Cys Asn Lys Leu Lys Ser Ser Asp Ala Tyr Lys Lys Ala
                       100                 105                 110
        Trp Gly Asn Asn Gln Asp Gly Val Val Ala Ser Gln Pro Ala Arg Val
                       115                 120                 125
        Val Asp Glu Arg Glu Gln Met Ala Ile Ser Gly Gly Phe Ile Arg Arg
        130                 135                 140
        Val Thr Asn Asp Ala Arg Glu Asn Glu Met Asp Glu Asn Leu Glu Gln
        145                 150                 155                 160
        Val Ser Gly Ile Ile Gly Asn Leu Arg His Met Ala Leu Asp Met Gly
                       165                 170                 175
        Asn Glu Ile Asp Thr Gln Asn Arg Gln Ile Lys Arg Ile Met Glu Lys
                       180                 185                 190
        Ala Asp Ser Asn Lys Thr Arg Ile Asp Glu Ala Asn Gln Thr Ala Thr
                       195                 200                 205
        Lys Met Leu Gly Ser Gly Thr Glu Asp Ala Lys Asn Ile Lys Lys Gly
        210                 215                 220
        Pro Ala Pro Phe Tyr Pro Leu Glu Asp Gly Thr Ala Gly Glu Gln Leu
        225                 230                 235                 240
        His Lys Ala Met Lys Arg Tyr Ala Leu Val Pro Gly Thr Ile Ala Phe
                       245                 250                 255
        Thr Asp Ala His Ile Glu Val Asn Ile Thr Tyr Ala Glu Tyr Phe Glu
                       260                 265                 270
        Met Ser Val Arg Leu Ala Glu Ala Met Lys Arg Tyr Gly Leu Asn Thr
                       275                 280                 285
        Asn His Arg Ile Val Val Cys Ser Glu Asn Ser Leu Gln Phe Phe Met
                       290                 295                 300
        Pro Val Leu Gly Ala Leu Phe Ile Gly Val Ala Val Ala Pro Ala Asn
        305                 310                 315                 320
        Asp Ile Tyr Asn Glu Arg Glu Leu Leu Asn Ser Met Asn Ile Ser Gln
                       325                 330                 335
        Pro Thr Val Val Phe Val Ser Lys Lys Gly Leu Gln Lys Ile Leu Asn
                       340                 345                 350
        Val Gln Lys Lys Leu Pro Ile Ile Gln Lys Ile Ile Met Asp Ser
                       355                 360                 365
        Lys Thr Asp Tyr Gln Gly Phe Gln Ser Met Tyr Thr Phe Val Thr Ser
        370                 375                 380
        His Leu Pro Pro Gly Phe Asn Glu Tyr Asp Phe Val Pro Glu Ser Phe
        385                 390                 395                 400
        Asp Arg Asp Lys Thr Ile Ala Leu Ile Met Asn Ser Ser Gly Ser Thr
                       405                 410                 415
        Gly Leu Pro Lys Gly Val Ala Leu Pro His Arg Thr Ala Cys Val Arg
                       420                 425                 430
        Phe Ser His Ala Arg Asp Pro Ile Phe Gly Asn Gln Ile Ile Pro Asp
                       435                 440                 445
        Thr Ala Ile Leu Ser Val Val Pro Phe His His Gly Phe Gly Met Phe
                       450                 455                 460
        Thr Thr Leu Gly Tyr Leu Ile Cys Gly Phe Arg Val Val Leu Met Tyr
        465                 470                 475                 480
        Arg Phe Glu Glu Glu Leu Phe Leu Arg Ser Leu Gln Asp Tyr Lys Ile
                       485                 490                 495
```

-continued

```
Gln Ser Ala Leu Leu Val Pro Thr Leu Phe Ser Phe Phe Ala Lys Ser
            500                 505                 510

Thr Leu Ile Asp Lys Tyr Asp Leu Ser Asn Leu His Glu Ile Ala Ser
        515                 520                 525

Gly Gly Ala Pro Leu Ser Lys Glu Val Gly Glu Ala Val Ala Lys Arg
    530                 535                 540

Phe His Leu Pro Gly Ile Arg Gln Gly Tyr Gly Leu Thr Glu Thr Thr
545                 550                 555                 560

Ser Ala Ile Leu Ile Thr Pro Glu Gly Asp Asp Lys Pro Gly Ala Val
                565                 570                 575

Gly Lys Val Val Pro Phe Phe Glu Ala Lys Val Val Asp Leu Asp Thr
            580                 585                 590

Gly Lys Thr Leu Gly Val Asn Gln Arg Gly Glu Leu Cys Val Arg Gly
        595                 600                 605

Pro Met Ile Met Ser Gly Tyr Val Asn Asn Pro Glu Ala Thr Asn Ala
    610                 615                 620

Leu Ile Asp Lys Asp Gly Trp Leu His Ser Gly Asp Ile Ala Tyr Trp
625                 630                 635                 640

Asp Glu Asp Glu His Phe Phe Ile Val Asp Arg Leu Lys Ser Leu Ile
                645                 650                 655

Lys Tyr Lys Gly Tyr Gln Val Ala Pro Ala Glu Leu Glu Ser Ile Leu
            660                 665                 670

Leu Gln His Pro Asn Ile Phe Asp Ala Gly Val Ala Gly Leu Pro Asp
        675                 680                 685

Asp Asp Ala Gly Glu Leu Pro Ala Ala Val Val Val Leu Glu His Gly
    690                 695                 700

Lys Thr Met Thr Glu Lys Glu Ile Val Asp Tyr Val Ala Ser Gln Val
705                 710                 715                 720

Thr Thr Ala Lys Lys Leu Arg Gly Gly Val Val Phe Val Asp Glu Val
                725                 730                 735

Pro Lys Gly Leu Thr Gly Lys Leu Asp Ala Arg Lys Ile Arg Glu Ile
            740                 745                 750

Leu Ile Lys Ala Lys Lys Gly Gly Lys Ser Lys Leu
        755                 760
```

N-END RULE PROTEASE ACTIVITY INDICATION METHODS AND USES THEREOF

CROSS REFERENCE TO RELATED APPLICATION

This application is a divisional of U.S. patent application Ser. No. 13/159,284, filed on Jun. 13, 2011, now U.S. Pat. No. 8,940,482, issued on Jan. 27, 2015, and is based upon and claims priority from U.S. Provisional Patent Application Ser. No. 61/354,041 entitled "N-End Rule Protease Activity Indication Methods and Uses Thereof," filed with the U.S. Patent and Trademark Office on Jun. 11, 2010, by the inventors herein and the specification of which is incorporated herein by reference in its entirety.

GOVERNMENT RIGHTS

This invention was made with government support under Grant No NO1-AI-30050 granted by the National Institute of Allergy and Infectious Diseases (NIAID). The government has certain rights in the invention.

FIELD OF THE INVENTION

This invention relates generally to Botulinum Toxin (BoNT) substrate C-terminal peptide fragments subject to proteasome degradation. More specifically to methods of using BoNT substrate C-terminal peptide fragments for measuring the activity of BoNTs and identification of BoNT inhibitors, diagnostic tests, and the interaction or presence of proteases in environmental samples by following the degradation of C-terminal markers subject to N-end rule degradation.

BACKGROUND OF THE INVENTION

Botulinum neurotoxins (BoNTs) are the most potent natural toxins known (1, 2). These include seven distinct serotypes (A-G) of BoNTs that block acetylcholine release from presynaptic terminals at neuromuscular junctions thereby causing flaccid paralysis (2, 3). The sequences of the seven serotypes of BoNTs are well known in the art. BoNTs are zinc metalloproteases comprising a 50 kD catalytic light chain (LC) linked by disulfide bonds to the 100 kD heavy chain (4). BoNTs transiently and reversibly inhibit synaptic transmission when their light chains cleave one of their target proteins at presynaptic termini. These proteins include Synaptosomal-Associated Protein of 25 kD (SNAP25), vesicle-associated membrane protein (VAMP) and syntaxin (4). The sequences of the BoNT substrates are well known. However, the duration of muscle paralysis varies among the serotypes. Both BoNT/A and BoNT/E target SNAP25. The duration of muscle paralysis from BoNT/A can last for several months whereas the effects of BoNT/E are relatively short-lived (5).

SUMMARY OF THE INVENTION

It is an object of the present invention to provide a cell based assay for assessing the activity of a Botulinum Neurotoxin (BoNT). The assay comprises providing a recombinant cell that expresses a BoNT substrate having a label at its C-terminus. The BoNT substrate generates a N-terminus fragment and a C-terminus fragment upon cleavage by the BoNT. The C-terminus fragment is degraded by the recombinant cell's ubiquitin proteasome pathway. The last step in the assay is measuring the expression of the label in the cell in the presence of the BoNT. In some embodiments of the invention, the BoNT is transported across the cell's membrane. In other embodiments, the BoNT is expressed by a vector inside the cell.

It is a further object of this invention to provide a cell based assay to distinguish between two BoNTs. The first step of the assay consists of providing a recombinant cell having a vector that expresses a protease substrate that is cleaved at a first site by a first protease generating a first C-terminus fragment and a first N-terminus fragment, and where said C-terminus fragment is degradable by the recombinant cell's ubiquitin proteasome pathway. The protease substrate is also cleaved at a second site by a second protease generating a second C-terminus fragment and a second N-terminus fragment, but said second C-terminus fragment is not degraded by the ubiquitin proteasome pathway. The recombinant cell is then contacted with the first protease and the label is measured. The cell is then contacted with the second protease and the label is measured. A comparison between the presence of the label with one protease and the label present with the second protease is used to determine the activity or presence of the protease that recognizes the substrate.

A method for evaluating Botulinum Toxin (BoNT) activity. The first step in the method consists of providing a BoNT substrate having a label at the BoNT substrate's C-terminus. In the second step, the BoNT substrate is placed in a solution selected from the group consisting of a cell free solution comprising components of a ubiquitin proteasome capable of degrading peptides or a cell based solution, wherein the peptide is expressed inside a cell having functional components of a ubiquitin proteasome. The BoNT substrate is then cleaved into at least two fragments, wherein at least one of said at least two fragments includes the label and is subject to degradation by the components of the ubiquitin proteasome. In the last step of the method the loss of signal from the label due to degradation of the fragment that includes the label is measured.

The method or claim 16, wherein the BoNT substrate is selected from the group consisting of synaptosomal associated protein of 25 kD (SNAP-25), a SNAP-25 isoform, vesicle-associated membrane protein (VAMP), a VAMP isoform, and peptides having at least 80% similarity to the foregoing and which have a cleavage sequence recognized by the protease.

A further object of the present invention is a method for identifying Botulinum Neurotoxin (BoNT) inhibitors. The first step of the method is to provide a recombinant cell comprising a vector that expresses a BoNT and a vector that expresses a BoNT substrate that upon cleavage by the BoNT generates a degradable C-terminal fragment having a label. The second step in the method is to express the BoNT and BoNT substrate. The third step consists of contacting said recombinant cell with a test molecule. The fourth step consists of measuring the presence of the first label and second label, wherein presence of the label. An increase in the signal from the label indicates inhibition of the BoNT.

BRIEF DESCRIPTION OF THE DRAWINGS

The numerous advantages of the present invention may be better understood by those skilled in the art by reference to the accompanying figures in which:

FIG. 3 shows the results of experiments showing that SNAP-25 C-terminus fragment is degraded after cleavage by BoNT/LC A.

DETAILED DESCRIPTION

Figure 1:
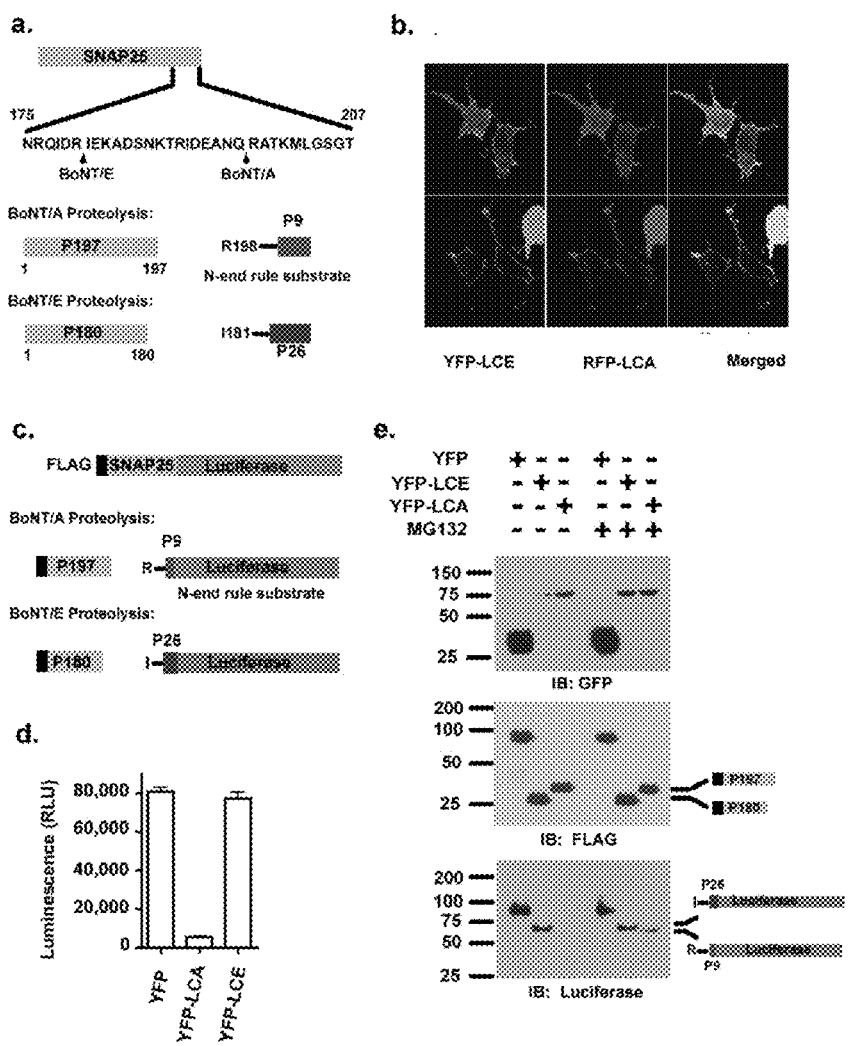
FIG. 1 shows the results of experiments showing SNAP-25 having a C-terminal labeled with Luciferase (SEQ ID NO. 2) and subject to N-end rule degradation in accordance with one embodiment of the present invention.

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

As utilized in this application, the terms "protein", "polypeptide" and "peptide" are well understood in the art and used interchangeably. Some of the embodiments of the present invention relate to peptides and variants of such peptides as understood by a person of ordinary skill in the art. A person of ordinary skill in the art will recognize that the certain embodiments of the present invention relate to the specific peptide sequences disclosed in the specification and also to variants such as fragments, analogs and/or derivatives of the disclosed peptide sequences. Variants of specific peptide sequences preferably retain at least one biological function or activity of the specific protein sequence.

The variants of the peptides may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (iv) one in which the polypeptide is fused with another polypeptide, e.g., GFP or luciferase, as further explained below. Variants also include peptides generated via proteolytic cleavage (including multi-site proteolysis) of an original sequence. Variants may be post-translationally or chemically modified. Any such variants are deemed to be within the scope of the invention by those skilled in the art.

As known in the art "similarity" between two peptides, as described by Davydov et al. (U.S. Pat. No. 7,608,682), is determined by comparing the amino acid sequence and its conserved amino acid substitutes of one peptide to the sequence of a second peptide which is incorporated herein by reference in its entirety. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to ubiquitylate via N-end rule pathway. The present invention includes protein sequences that are at least 60%, 65%, 70%, 72%, 74%, 76%, 78%, 80%, 90%, or 95% similar or identical to an amino acid sequences described herein. Still within the scope of the invention are preferred segments of interest within the peptides recognized by various proteases. Such segments include fragments of at least 10, 25, 50, 100, 150 or 200 amino acid residues, which are recognized by a protease and cleaved. A person of ordinary skill in the art would recognize that the present invention includes variants of the substrates described herein, which are degradable by the N-end rule ubiquitylation pathway.

Other embodiments of the invention relate to products of interactions of these peptides (or variants thereof) with other components of one or more biological pathways. Certain further embodiments relate to methods of identifying biologically active substances that modulate, inhibit, or enhance the activity of these peptides, the peptides' variants, or enzymes that interact with the peptides. The peptides also relate to the use of the active substances in pharmaceutical compositions. Other embodiments of the invention relate to diagnostic methods that involve measuring these peptides, their associated biological activity, or the biological activity of the enzymes or proteases that interact with the peptides. Furthermore, other embodiments of the invention relate to reagents, kits and assay compositions, which assist in carrying out the methods described below.

In accordance with one embodiment of the present invention, the applicants have identified peptide substrates of proteases that are subject to the N-end rule. As utilized in this application, peptide residues that signal degradation are referred to as N-degrons. Residues that promote degradation are called "destabilizing" residues and residues that do not promote degradation are called "stabilizing" residues. Thus, N-degrons are the "destabilizing" in the peptide fragment. The applicants have identified various protease fragments that are degraded by the ubiquitin proteasome pathway inside cells.

As provided in certain embodiments of the present invention, a protease cleaves its peptide substrate generating two fragments each having a new N-terminal and a new C-terminal. The C-terminal fragment is subject to N-end rule degradation by the ubiquitin degradation pathway. As described in this application, a peptide substrate is a peptide that a specific protease recognizes and cleaves generating two or more fragments, of which at least one has an N-degron and is degraded by the ubiquitin proteasome system of a cell. It is contemplated that, if the protease generates more than two fragments, at least one of such fragments contains an N-degron.

In one embodiment of the present invention, the peptide substrate of a protease has a tag or label at its C-terminal. The terms "tag", "label" or "indicator" are used interchangeably in this application and refer to reporter molecules that are attached to a peptide and allow for detection of the peptide or peptide fragment in a sample. Labels used in some embodiments of the present invention may comprise a radioisotope, a fluorescent (including fluorescence polarization, yellow fluorescent protein (YFP), blue fluorescent protein (BFP), green fluorescent protein (GFP), red fluorescent protein (RFP) and fluorescing mutants thereof), phosphorescent, luminescent (including firefly, *Renilla*, and *Gaussia* luciferases), chemiluminescent and/or electro-chemiluminescent (ECL) compound, an enzyme, or an enzyme co-factor as a label moiety, including binding species recognized by preferably labeled binding partner (e.g., biotin, streptavidin, epitope tags, affinity tags (e.g., His6), fluorescein, hapten, immunogen, GST and/or GFP), which are well recognized in the art. Labeling the C-terminal of the protease substrate generates a labeled degradable fragment. In further embodiments of the present invention, the protease substrate has one label at its N-terminal and a second label at its C-terminal. The labels at each terminal end are used to determine the presence of each fragment in a sample.

It is contemplated that FRET pairs may also be used as labels for the peptide substrate. FRET assays rely on the proximity between the labels on each end of the labeled peptide. The method relies on the change in signal that results from the cleavage of the peptide substrate and separation of the two labels. Traditional FRET assays are not always reliable because the cleaved fragments remain in the solution or mixture and sometimes lead to false negative results. Both cleaved fragments remains in the solution mixture and continue to interact leading to results that appear to show that no cleavage took place. The N-end rule degradation of one of the fragments, as described herein, solves this problem by completely removing one member of the FRET pair from the solution leading to accurate results.

In accordance with one embodiment of the present invention, a method for measuring the presence or level of activity of the protease that is specific to the protease substrate is described. In a first step of the method, the protease substrate is provided in a mixture that is capable of degrading one of the fragments cleaved by the protease. In a second step of the method, a protease is added to the mixture. In a third step the presence of the label is measured. In an alternative embodiment, the presence of the label is measured before the protease is added to the mixture. In yet a further alternative embodiment the method, the protease substrate has a label in each its N-terminal and its C-terminal. The second step of this alternative embodiment, the protease is added to the mixture and in the third step the difference between the presence of the N-terminal label and the C-terminal is measured.

Methods for measuring the presence of a label are well understood in the art. When radioactive labels are used, for example, cell lysate is run in gels and the radioactive label will indicate bands in which the labeled target is located. In such example, the lack of the band when compared to a control indicates loss of the label. In other examples, a western blot using antibodies specific for the label are used. Again, disappearance of a band in the western blot when compared to a control indicates degradation of the fragment. In live cell assays, on the other hand, bioluminescent, fluorescent, and other labels are used to evaluate the presence of a label in real time. In the live cell assay, as described herein, the label is measured before a protease has acted on the substrate by fluorescent micrography. Evaluating the cells at different times provides a system to determine whether the label is expressed and how it continues to be expressed after a period of time. For example, a control without expression of a protease shows that the label continues to be present after 24 hours. On the other hand, after the protease is expressed or allowed to interact with its substrate, the fluorescent label is no longer present. Yet a further example of measurements of the presence of the label include luminometers to measure the activity of luciferases. A person of ordinary skill in the art would recognize that there are other tools for measuring the presence of labels in a mixture and that such methods are within the scope of the present invention.

In yet a further embodiment of the method, the labeled protease substrate is produced from a plasmid DNA in a transcription-translation reaction mixture containing rabbit reticulocyte lysate and a RNA polymerase (such as SP6 or T7) as described by Davydov et al. (U.S. Pat. No. 7,608,682). The peptide substrate is produced in the absence of the peptide substrate specific protease. In one alternative embodiment, the protease is added to the mixture and then the presence of the label is measured. In a further alternative embodiment, the presence of the label is measured or ascertained before the protease is added and the decrease in the presence of the label is measured after addition of the protease. In another embodiment of the method, where two labels are used, the relative change in the label in the degradable fragment in relation to the label of the N-terminal fragment is measured to determine the activity of the protease.

In a further embodiment of the present invention, the method described above is utilized to determine the presence of a target protease in a sample. For example, the method is used to test environmental samples at a suspected site of exposure to a toxic protease. In such an embodiment, the peptide substrate mixture described above is placed in a multi well array where the label signal has been measured. Samples are then added to each well and disappearance of the degradable fragment is measured. In an alternative method, the difference between the label in the N-terminal and the C-terminal of the protease substrate is measured. An increase in the difference in the ration of N-terminal label to C-terminal label indicates the activity of the protease.

Another embodiment of the method described above is utilized to identify protease inhibitors. The method comprises a first step of the labeled protease substrate in a mixture capable of degrading N-end rule degradable fragments. In a second step, a proposed inhibitor molecule or a library is added to the mixture. In a third step, the degradation of the fragments is evaluated as described above either for single labeled or double labeled substrates. In a fourth step, the positive results are screened for proteasome inhibition activity by methods well recognized in the art. Those results that do not inhibit the proteasome are BoNT inhibitors. By way of example, the target inhibitor may be screened using a cell line that degrades a proteasome substrate with a specific label, one such examples includes GFP-CL-1, if the inhibitor acts on the proteasome pathway, the GFP-CL-1 signal will remain.

In an alternative embodiment, the method is utilized to identify proteasome component inhibitors. In order to differentiate protease inhibitors from ubiquitin proteasome pathway inhibitors, a candidate inhibitor is tested in the presence of the protease and protease substrate and also in the presence of ubiquitin proteasome sensitive substrate, which is not subject to cleavage by the protease. By way of non-limiting example, the inhibitor is tested in the presence of BoNT/LC A and the SNAP-25 construct described below and in the presence of the ubiquitin proteasome peptide marker GFP-CL-1. If the inhibitor is specific for BoNT/LC A the SNAP-25 construct will not be cleaved and the label signal will remain constant; on the other hand, the label signal for the GFP-CL-1 construct will disappear as it is degraded by the proteasome. Other ubiquitin proteasome markers include GFP-CL1, Ub$^{G76V}$-GFP, Ub-R-GFP. A person of ordinary skill in the art will recognize that the label may be selected from the group consisting of GFP, β-galactosidase, and luciferase.

A further embodiment of the present invention provides an engineered cell line that is capable of transporting target protease into its cytoplasm. The cell line expresses the peptide substrate of the protease with a label at its C-terminus. The following cell types are appropriate for expression of the peptide substrate: HEK293, CHO, BHK, HeLa, COS, and neuroblastoma cells such as Neuro2A, M17, PC12, and N18. A person of ordinary skill in the art will recognize that other cell types that allow for either expression of the plasmids for the various peptides described herein are within the scope of the present invention. Similarly, cell types that recognize and transport a protease across the cellular membrane allowing it to cleave the protease substrate expressed within the cell are within the scope of the present invention.

In a further embodiment, the peptide substrate comprises a label on both its C-terminus and its N-terminus. The peptide substrate permits the measurement of the label by bioluminescence, chemiluminesence, fluorescence, or any other methods as recognized by those skilled in the art as described above.

In one embodiment of the present invention, the cell line is engineered for constitutive expression of the peptide substrate causing the label to be measurable in the absence of a protease. In an alternative embodiment, peptide substrate expression is regulated as understood by a person of ordinary skill in the art. In one non-limiting example, the peptide is introduced in the cell by an inducible vector. The inducible vector only expresses the peptide if the inducer is present. Such inducible vectors are well recognized in the art. Once the peptide substrate is expressed, the cell is allowed to reach a steady state of expression allowing measurement of the peptide labels and the recombinant cell is used to test the activity of the protease that specifically cleaves the substrate.

In one embodiment of a method of the present invention, the target protease is presented to the engineered cell line and its effect on the peptide substrate signal is measured. In one embodiment of the present invention where the protease substrate has a single label, a reduction in the signal is measured once the steady state is reached. A reduced level of label indicates an active protease. In the alternative, when the peptide substrate includes two labels, the difference in the ratio of N-terminal label to that of the C-terminal label is measured. A decrease in the ratio of C-terminal label to N-terminal label indicates the activity of the protease. In a further embodiment, the cell line is utilized to test environmental samples for the presence of a specific protease.

In an alternative embodiment a cell is provided that is capable of transporting a protease inside its cytoplasm. The cell is transfected with a vector that includes the peptide substrate for the protease. The vector expresses the peptide substrate, which is cleaved by the protease resulting in an N-terminal fragment and a C-terminal fragment. The peptide substrate as described above has a label on the N-terminal fragment and the C-terminal fragment. When the protease cleaves the peptide substrate, one of the fragments is degraded. The ratio of C-terminal label to N-terminal label indicates the activity of the protease.

In one further embodiment of the present invention, the activity of two proteases that cleave the same substrate at different regions is measured where one of the segments is subject to N-end rule degradation. In such embodiment, the loss in signal indicates the presence of the protease that generates a degradable fragment. It is also possible to compare the results of the differences between the two proteases if the peptide substrate is labeled with FRET pairs that are separated by the cleavage site. The traditional FRET assay cannot distinguish between the two proteases, while the N-end rule method described in this application does.

The loss in signal due to the degradation of the degradable fragment results in a larger change in signal than that of due to the simple cleavage of the peptide fragment separating each component of the FRET pair. In yet a further embodiment, the specificity of the protease is ascertained by comparing the decrease in C-terminal label to N-terminal label ratio when compared to a known control ratio of C-terminal label to N-terminal label.

One significant advantage of the embodiments of the present invention is the ability to differentiate loss of signal in a cell base system due to specific cleavage by the protease from the loss of signal due to other factors such as cell death.

In yet a further embodiment of the present invention, a method for identifying protease inhibitors is provided. In the first step of the method, a cell line for carrying out the assay is provided. The cell is engineered to express a peptide substrate having at least one label on its C-terminus and subject to the degradation through the ubiquitin proteasome pathway. The cell is further engineered to express a second peptide that is labeled and subject to degradation by the ubiquitin proteasome pathway but which is not a substrate of the protease. In the second step of the method, a protease inhibitor candidate is placed in contact with the cell. Depending on the size of the inhibitor, it may be incorporated into the cell passively or actively. On a third step of the method the expression of the label from the first peptide and the second peptide are measured. Presence of the protease substrate label only indicates that the inhibitor specifically inhibits the protease.

The applicants have shown that BoNT/LC A cleaves SNAP-25 (6) generating a degradable fragment. Vesicle Associated Membrane Protein (VAMP, also referred to as Synaptobrevin, which sequence is found at GebBank: CAA88760; NCBI Reference Sequence: NP_055047) is cleaved by BoNT/LC B, BoNT/LC F, and Tetanus Toxin (6) generating a degradable fragment. The third BoNT substrate is Syntaxin 1, which is cleaved by BoNT C1, but cleavage does not generate a degradable substrate. The applicants observed that BoNT/LC E cleaves SNAP-25 but it does not generate a degradable fragment.

Peptides comprising the entire sequence of SNAP-25 or VAMP will generate degradable fragments in accordance with one embodiment of the present invention. Fragments of SNAP-25 or VAMP and variants of SNAP-25 or VAMP will also generate degradable fragments provided the cleavage sequence in SNAP-25 or VAMP and recognized by the various BoNT/LCs remains intact. Such variants include SNAP-25 or VAMP isoforms, and other peptides having a similarity of 80% to the known SNAP-25 of VAMP peptides that have cleavage sequences recognized by the various proteases.

The applicants have demonstrated that the cleavage of the SNAP-25 by BoNT/A is followed by complete degradation of the SNAP-25 P9 C-terminal fragment in cells. The applicants have shown that the C-terminal fragment generated by BoNT/A cleavage is rapidly degraded. The change in the immunofluorescence of the N-terminal fragment to that of the respective C-terminal fragment in the presence or absence of BoNT/A indicates the activity of the protease. The P9 fragment from BoNT/A cleavage was rapidly degraded and is unlikely to accumulate to any significant levels in cells.

Applicants have also demonstrated that the C-terminus of a SNAP-25 after cleavage with BoNT/LC A is completely degraded in other constructs. As shown in FIG. 3, for example, fluorescent micrographs of 293 FT cells co-transfected with SBP-CFP-SNAP25-Venus-BD-NFkB and BoNT/LC A plasmids shows that the C-terminal fragment containing the Venus fluorescent protein is degraded after cleavage. FIG. 3(a) shows that the N-terminal fragment that contains CFP is present after 24 hours. FIG. 3(b) shows that the C-terminal fragment containing the Venus YFP is not present signaling degradation. FIG. 3(c) further shows that the CFP-SNAP-25-VENUS-BD-NFkB (see Oyler et al., U.S. patent application Ser. No. 12/962,610, which is incorporated herein by reference in its entirety) peptide is cleaved. Lane 3 shows the construct as a 125 kDa band, while lane 4 shows only a 57 kDa fragment after cleavage, which corresponds to the N-terminal fragment of SNAP-25.

Results

As shown in FIG. 1a, SNAP25 results in proteolytic fragments generated from BoNT/A and BoNT/E. FIG. 1(b) Co-localization of BoNT/E and BoNT/A light chains in neuronal cells, which helped confirm that the N-end rule degradation was the reason for the decrease in signal from the labeled SNAP-25. FIG. 1(c) shows the design of a luciferase reporter for BoNT proteolytic activity in accordance with one embodiment of the present invention. FIG. 1(d) shows the effect of N-end rule degradation in a bioluminescence assay. Cells were transfected with luciferase reporter and YFP, YFP-LCE or YFP-LCA and luminescence measured with a luminometer 36 h post-transfection. Data shown are mean±SEM (n=3; p<0.01 YFP-LCA compared to YFP) in arbitrary relative luminescence unit (RLU). The results show that there is a significant decrease in signal for the SNAP-25 YFP-LCA sensitive fragments. FIG. 1(e) shows the effect in cells transfected with luciferase reporter and the indicated plasmids. Cells were treated with DMSO or 20 μM MG132 overnight and lysates probed with indicated antibodies.

The high A/T content of *Clostridium* genes makes their expression in mammalian cells challenging. To overcome this and study the basis for toxin persistence, we constructed cDNAs encoding BoNT/A LC (LCA) and BoNT/E LC (LCE) with codons optimized for mammalian expression. To help visualize the localization of LCs in living cells, they were fused to yellow (YFP) or red fluorescent protein (RFP). We co-transfected YFP-LCE and RFP-LCA in N18 neuroblastoma cells to directly compare the sub-cellular localization of LCA and LCE. LCA is primarily localized to the plasma membrane when expressed in neuroblastoma cells (FIG. 1b). LCA can also be found in some intracellular membranes and vesicles. Interestingly, LCE has a similar distribution in neuroblastoma cells (FIG. 1b). Confocal imaging showed that YFP-LCE and RFP-LCA are, in fact, co-localized in these cells (FIG. 1b). This result suggests that persistence of BoNT/A LC cannot be explained by a difference in steady state sub-cellular localization relative to BoNT/E LC.

Figure 2:
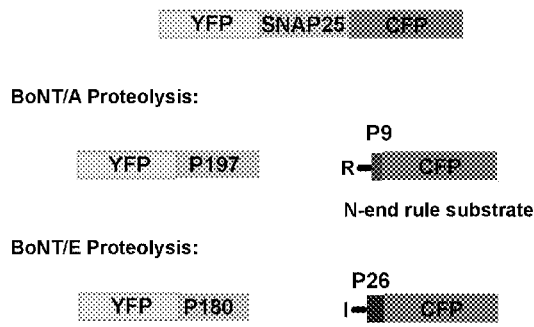
FIG. 2 shows the results of experiments showing SNAP-25 having a C-terminal labeled with CFP.
Figure 2:
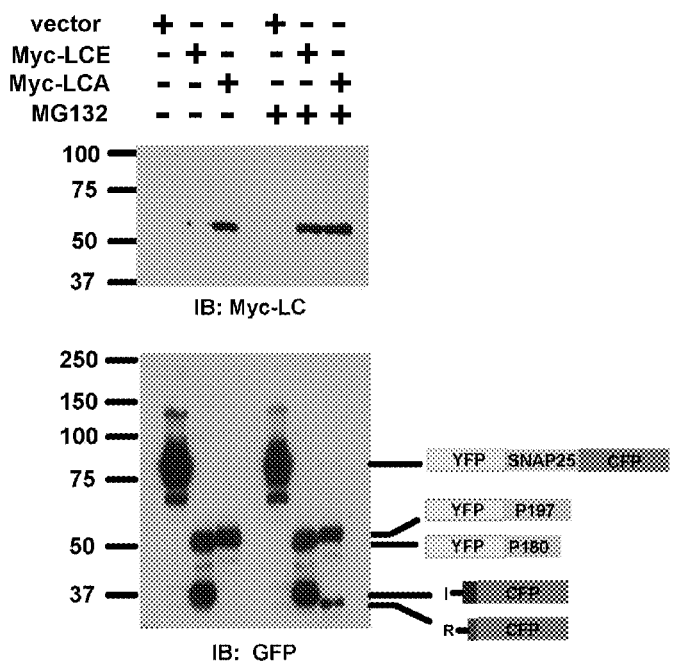

To address the possibility that persistence might result from increased stability of the shorter BoNT/LC A-generated C terminal fragment of SNAP25, we constructed a reporter consisting of luciferase fused to the C-terminus of FLAG-tagged murine SNAP25 (FIG. 1c). BoNT/A cleaves the construct to generate a P197 and a C-terminal product corresponding to P9 fused to luciferase. Applicants observed that the P9 containing fragment generated by BoNT/A cleavage bears a N-terminal Arg (R197 of SNAP25) and was rapidly degraded. In contrast, BoNT/E cleavage yields the P180 fragment and a C-terminal product that is relatively stable. Consistent with this prediction, co-transfection of the reporter construct with BoNT/A LC resulted in more than 10-fold reduction in luciferase activity whereas co-expression with BoNT/E LC resulted in only small changes in luciferase activity (FIG. 1d). Immunoblotting with an antibody against the N-terminus of the construct confirmed proteolysis of the full length SNAP25-luciferase reporter by YFP-LCA and YFP-LCE to generate two fragments (FIG. 1e, middle panel). The N-terminal fragments appeared relatively stable compared to the full-length reporter. Notably, the C-terminal fragment produced by BoNT/A proteolysis was barely detectable but accumulated in the presence of MG132, an inhibitor of the proteasome (FIG. 1e, lower panel). The rapid loss of the P9 containing fragment from BoNT/A proteolysis is not simply caused by fusion with luciferase as fusion with other protein (CFP) yields similar results (FIG. 2). These results not only confirm the activities of our recombinant BoNT/A and BoNT/E LCs in cells but also demonstrate that the P9 fragment generated by BoNT/A is short-lived and is a good indicator of BoNT/A activity. As a result, the assay is useful in differentiating BoNT/LC A from BoNT/LC E activity.

Materials and Methods

Plasmids

We constructed synthetic genes for BoNT/A and E light chains (LCs) using preferred codon usage for *E. coli* and mammals. Murine SNAP25 was generated by PCR and subcloned into pcDNA3.1(+) FLAG vector. Luciferase was subcloned into pcDNA3.1(+) SNAP25 to construct the reporter. The SNAP-25-Luc nucleotide sequence is provided as SEQ ID. No. 1 and the aminoacid sequence of the SNAP25-Luc construct is provided as SEQ ID No. 2. To construct ubiquitin ligases targeting BoNT LCs, we first generated the SNAP25 mutant (SNC) resistant to both BoNT/A and E proteolysis for which the nucleotide is provided as SEQ ID No. 3 and the peptide sequence is provided as SEQ ID No. 4.

Synthetic genes for botulinum neurotoxin serotypes A and E (BoNT/A and /E) light chains (LCs) were generated de novo using preferred codon usage in *E. coli* and mammals. Briefly, oligonucleotides of 50-60 nt were designed in pairs to introduce overlapping regions of 12 nt at their opposing ends. These pairs were extended and amplified using PCR to create fragments of ~100 nt, which then were used as building blocks in successive rounds of PCR with primers having 12 nt overlaps with the ends of the prior PCR amplification. This type of "overlap extension" PCR was used to create the entire synthetic gene. After verification by DNA sequencing, BoNT/A and /E LCs were subcloned into pEYFP-C1, pEGFP-C1, mRFP-C1, pcDNA3.1+, or pCMVTag2C using the unique XhoI and ApaI sites. Tetracyclineinducible constructs were generated by subcloning GFP-LCA or -LCE in pcDNA5/TO/Frt. To generate the reporter construct, FLAG-murine synaptosomal-associated protein 25 (SNAP25) was generated by PCR and subcloned into pcDNA3.1+ vector between the BamHI and XhoI sites. A KpnI site was engineered before the stop codon of SNAP25 and allowed insertion of luciferase or other reporters between the KpnI and XhoI sites. To construct ubiquitin ligases targeting BoNT LCs, we first generated SNAP25 noncleavable mutant (SNC), which contains the mutations (D179K, R198T) and is resistant to both BoNT/A and /E proteolysis (QuickChange Kit; Invitrogen).

Cell Culture and Transfection. Cell lines were cultured in standard culture medium in a 37° C., 5% CO2 incubator. HEK293 cells were grown in DMEM containing 10% (vol/vol) FBS, 2 mM glutamine, and 2% penicillin-streptomycin. HEK-Flp-in/T-REX/293 cells (Invitrogen) were grown in DMEM supplemented with 10% (vol/vol) tetracycline-free FBS (Clontech), 2 mM glutamine, 2% penicillin-streptomycin, 100 μg/mL zeocin, and 15 μg/mL blasticidin. Human neuroblastoma SH-SY5Y cells were cultured in DMEM/F12 medium containing 10% (vol/vol) FBS, 2 mM glutamine, and 2% penicillin/streptomycin. N18 cells were cultured in DMEM supplemented with hypoxanthine, aminopterin, thymidine medium, 10% (vol/vol) FBS, 2 mM glutamine, 2% penicillin/streptomycin. Murine neuroblastoma Neuro2a cells were cultured in EMEM containing 10% (vol/vol) FBS. Cell culture reagents were obtained from Invitrogen. Transfections were carried out using Lipofectamine 2000 (Invitrogen) or HiPerfect (Qiagen).

Metabolic Labeling. Pulse-chase analysis was performed 30 h after transfection. Briefly, cells were starved for 1 h in methionine/cysteine (Met/Cys)-free medium and labeled for 45 min with 100 µCi/mL [35S]-Met/Cys (MP Biologicals). After labeling, cells were washed three times with PBS and cultured in chase medium containing a 10-fold excess of unlabeled Met. At the indicated times, cells were washed three times with PBS and lysed with RIPA lysis buffer [50 mM Tris (pH 7.4), 150 mM NaCl, 1% (vol/vol) Triton X-100, 0.5% (wt/wt) sodium deoxycholate, 0.1% (wt/wt) SDS, 50 µM MG132, and protease inhibitors (Roche)]. YFP-LCs were immunoprecipitated with GFP antibodies. After extensive washing with lysis buffer, immunoprecipitated proteins were eluted in 2×sample buffer, resolved by SDS PAGE, and processed for analysis on a STORM phosphoimager and analyzed with ImageQuant software (GE Healthcare Life Sciences).

Antibodies and Reagents. We purchased rabbit polyclonal antibody against GFP and RFP from Clontech; HA antibody from Roche; Luciferase antibody from Promega; FLAG M2 antibody from Sigma; and monoclonal antibodies to GFP, TRAF2, and ubiquitin from Santa Cruz. Myc antibody was obtained from culture supernatant of 9E10 hybridoma. Unless indicated otherwise, all chemicals were obtained from Sigma-Aldrich.

Fluorescence Microscopy. Thirty hours after transfection, cells were fixed in 4% paraformaldehyde for 10 min and washed with PBS before imaging on a Zeiss LSM 510. All images were minimally processed for presentation.

Luciferase Assay. Luciferase assays were performed 36 h after transfection using the Dual-Luciferase reporter kit (Promega) according to the manufacturer's recommendations.

REFERENCES

The following references cited within the body of the specification are incorporated herein by reference in their entirety.
1. Simpson, L. L. (2000) *Biochimie* 82, 943-53.
2. Habermann, E. & Dreyer, F. (1986) *Curr Top Microbiol Immunol* 129, 93-179.
3. Jahn, R. & Niemann, H. (1994) *Ann NY Acad Sci* 733, 245-55.
4. Montecucco, C. & Schiavo, G. (1995) *Q Rev Biophys* 28, 423-72.
5. Eleopra, R., Tugnoli, V., Rossetto, O., De Grandis, D. & Montecucco, C. (1998) *Neurosci Lett* 256, 135-8.
6. Cesar Montecucco and Giampietro Schiavo, (1994), *Molecular Microbiology* 13(1), 1-8.

What is claimed is:

1. A cell based assay to distinguish between two proteases, comprising:

providing a recombinant cell, the recombinant cell having a vector that expresses a protease substrate having a label at its C-terminus, wherein said substrate is cleaved at a first site by a first protease generating a first C-terminus fragment and a first N-terminus fragment, and where said C-terminus fragment is degradable by the recombinant cell's ubiquitin proteasome pathway;

the protease substrate is also cleaved at a second site by a second protease generating a second C-terminus fragment and a second N-terminus fragment, and where said second C-terminus fragment is not degraded by the ubiquitin proteasome pathway;

contacting the recombinant cell expressing the protease substrate with the first protease and measuring the presence of the label;

contacting the recombinant cell expressing the protease substrate with the second protease and measuring the presence of the label;

comparing the difference in the presence of the label after contact with the first protease to the presence of the label after contact with the second protease.

2. The cell based assay of claim 1, wherein the two proteases are BoNT/LC A and BoNT/LC E and the protease substrate is SNAP-25.

3. The cell based assay of claim 1, further comprising the step of contacting a sample having one or more cells with a sample containing an unidentified protease; identifying the unidentified protease by measuring the degradation of the label in the cells.

4. The cell based assay of claim 1, wherein the contacting step comprises exposing the recombinant cell to said first or second protease in a sample or inducing the production of said first or second protease in the cell from a vector.

* * * * *